United States Patent [19]
Smith et al.

[11] Patent Number: 6,097,482
[45] Date of Patent: Aug. 1, 2000

[54] HIGH SPEED FLAW DETECTING SYSTEM FOR REFLECTIVE MATERIAL

[75] Inventors: Barry Scott Smith, Hopewell; Michael J. Mullins, Chesterfield, both of Va.; Roy E. Van Derlinden, Frederick, Md.; Donald L. Irvin, Leesburg, Va.

[73] Assignee: Philip Morris Incorporated, New York, N.Y.

[21] Appl. No.: 09/327,531

[22] Filed: Jun. 8, 1999

[51] Int. Cl.[7] .................................................. G01N 21/00
[52] U.S. Cl. .................................. 356/237.1; 356/237.3; 356/239.1; 250/237 R
[58] Field of Search .............................. 356/237.1, 237.2, 356/237.3, 237.4, 237.5, 239.1, 239.3, 239.7, 239.8; 250/237 R, 227.29

[56] References Cited

U.S. PATENT DOCUMENTS

| | | |
|---|---|---|
| 3,762,496 | 10/1973 | Milberger et al. . |
| 3,779,843 | 12/1973 | Knapp . |
| 3,780,570 | 12/1973 | Collins . |
| 3,937,065 | 2/1976 | Milberger et al. . |
| 4,162,126 | 7/1979 | Nakagawa et al. ................... 356/237.2 |
| 4,377,340 | 3/1983 | Green et al. ........................... 356/237.3 |
| 4,509,369 | 4/1985 | Kuljis et al. . |
| 4,519,245 | 5/1985 | Evans . |
| 4,577,337 | 3/1986 | Light . |
| 4,807,996 | 2/1989 | Ginnis et al. . |
| 4,924,182 | 5/1990 | Vernon et al. . |
| 4,936,649 | 6/1990 | Lymer et al. . |
| 4,939,469 | 7/1990 | Ludwig et al. . |
| 4,976,150 | 12/1990 | Deka . |
| 5,001,932 | 3/1991 | Light et al. . |
| 5,046,363 | 9/1991 | Moore . |
| 5,067,352 | 11/1991 | Floret . |
| 5,094,108 | 3/1992 | Kim et al. . |
| 5,146,289 | 9/1992 | Newman . |
| 5,164,971 | 11/1992 | Peyret et al. . |
| 5,203,942 | 4/1993 | DeCook et al. . |
| 5,231,536 | 7/1993 | Wilt et al. ........................... 250/237 R |
| 5,265,475 | 11/1993 | Messinger et al. . |
| 5,289,785 | 3/1994 | MacPherson et al. . |
| 5,300,183 | 4/1994 | DeCook . |
| 5,376,793 | 12/1994 | Lesniak . |
| 5,444,241 | 8/1995 | Del Grande et al. . |
| 5,469,294 | 11/1995 | Wilt et al. ........................... 250/237 R |
| 5,585,918 | 12/1996 | Takeuchi et al. ..................... 356/237.1 |
| 5,943,127 | 8/1999 | Feldman et al. ..................... 356/237.2 |

*Primary Examiner*—Hoa Q. Pham
*Attorney, Agent, or Firm*—Burns, Doane, Swecker & Mathis, L.L.P.

[57] ABSTRACT

An apparatus for the detection of surface flaws in material having a surface which is partially reflective includes at least one light source arranged to direct incident light on a surface of an at least partially reflective material, and a light detector disposed above the surface of the material. The light detector and the at least one light source are arranged relative to each other such that, in the absence of a surface flaw in the material, substantially no light from the at least one light source is detected by the light detector and, in the presence of a surface flaw in the material, light from the at least one light source is reflected off of the flaw and into the detector.

26 Claims, 4 Drawing Sheets

HIGH SPEED FLAW DETECTING SYSTEM FOR REFLECTIVE MATERIAL

BACKGROUND AND SUMMARY OF THE INVENTION

The present invention relates to an optical detection device for use in examining a surface of material for a flaw. More specifically, the invention contemplates large-scale, high-speed examination of surfaces which are at least in part reflective for flaws; the reporting of such flaws and the rejection of flawed materials.

The high-speed nondestructive analysis of produced bulk material for quality assurance reasons has been a concern for industry for many years. Without proper control and quality checking, a product can end up at the final consumption location be found lacking in quality, and require return and/or replacement.

Such a late-discovered defect is quite expensive from a manufacturer's standpoint, involving shipping costs, administrative costs, and perhaps most important to a company that strives to achieve a reputation for consistent quality, a loss of customer goodwill.

Many different methods for such nondestructive analysis have been proposed. For example, Peyret et al U.S. Pat. No. 5,164,971 discloses the use of radiographic and tomographic data obtained by an x-ray or gamma-ray source-detector apparatus. An angular rotation of the object results in accommodation of data which is analyzed to reconstruct sections of the object.

Messinger, U.S. Pat. No. 5,265,475 provides for a fiber-optic strain sensor for determining the integrity of critical bonded joints in aerospace applications (including laminates) by embedding a strain sensitive fiber optic cable within the joint or laminate.

Del Grade et al U.S. Pat. No. 5,444,241 discloses a method of detecting flaws in structures by the application of heat to those structures, then scanning the structure for two different wavelengths, obtaining the data as images, and analyzing the images for flaws.

Newman, U.S. Pat. No. 5,146,289 discloses the detection of defects in, e.g. laminates, by the air-coupled acoustic excitation of objects, and use of an interferometer to detect images of the object formed by light reflected from the object. The images are compared and differences provide information on the condition of the object.

Kim et al U.S. Pat. No. 5,094,108 discloses a contact ultrasonic transducer which focuses ultrasonic waves on a point to detect flaws on a surface or subsurface of a substrate. U.S. Pat. No. 5,046,363 also describes the use of acoustic waves to check for voids in a dis-attach layer of integrated circuit packaging. U.S. Pat. No. 5,001,932 discloses a nozzle assembly for discharging water onto a structure so as to prepare it for ultrasonic testing.

Each of these methods or apparatus provides a complex solution to checking manufactured or laminate products for flaws by analysis of collected data, either by complex imaging techniques or algorithmic manipulation of data. Such techniques are not well-adapted to high-speed analysis of great quantities of material.

It, therefore, is an object of the present invention to provide a method of analyzing large quantities of material for defects.

It is a further object of the present invention to provide an apparatus which is capable of analyzing large quantities of material for defects at high speed.

It is yet another object of the present invention to provide a simple optical device which performs the above objects utilizing light scattering or pass through qualities of the surfaces to be analyzed.

The present invention provides a method and apparatus for scanning large surface areas at high speed. A sheet material, preferably a material with a large surface area, is passed along a planar region at a preselected speed. The material is illuminated by a light source such as a fiber optic light source. A detector, such as a ccd linear array, is strategically located such that no light is received by the detector when the surface is flaw-free. For material without flaws, light which is reflected is uniformly reflected, resulting in substantially no scatter of light that might be detected by the detector. In the presence of a flaw, there is sufficient light scatter to be detected by the detector.

In accordance with one aspect of the present invention, an apparatus for the detection of surface flaws in material having a surface which is partially reflective is provided. The apparatus includes at least one light source arranged to direct incident light on a surface of an at least partially reflective material, and a light detector disposed above the surface of the material. The light detector and the at least one light source are arranged relative to each other such that, in the absence of a surface flaw in the material, substantially no light from the at least one light source is detected by the light detector and, in the presence of a surface flaw in the material, light from the at least one light source is reflected off of the flaw and into the detector.

In accordance with another aspect of the present invention, an apparatus for the detection of surface flaws in a reflective material is provided. The apparatus includes a plurality of fiber optic light sources arranged relative to a reflective material to illuminate the surface of the material, a line-scan camera facing a surface of the material, and light baffles separating the light sources and the camera. When the material is moved relative to the camera and no flaw in the material is present, light from the light sources is reflected off of the material and is blocked by the baffles such that no light from the light sources is detected by the detector. When a flaw in the material is present, light from the light sources is reflected off of the flaw such that the baffles to not block the reflected light and the reflected light is detected by the detector.

In accordance with yet another aspect of the present invention, a method for the detection of flaws in material is provided. According to the method, a material having a reflective surface is moved in a direction parallel to the reflective surface. At least one light source and a light detector are arranged relative to each other, and light is emitted from the at least one light source and onto the reflective surface as the reflective surface is moved such that, when no flaw is present in the reflective surface, no light is detected by the light detector. Light reflected from one or more flaws on the reflective surface is detected with the detector.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION

Figure 1:
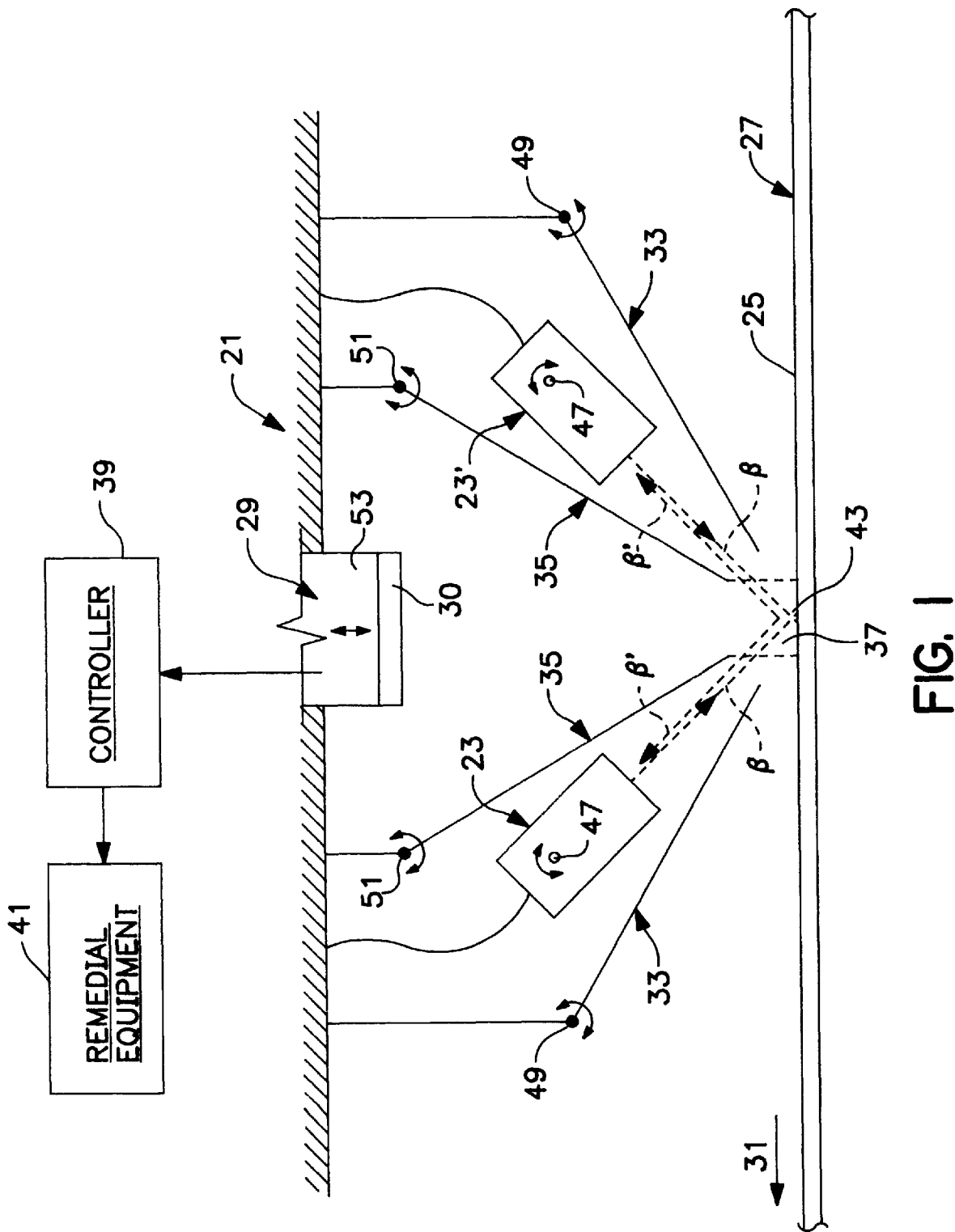
FIG. 1 is a schematic, partially cross-sectional, side view of an apparatus according to the present invention showing normal operation with material having no flaws.
Figure 2:
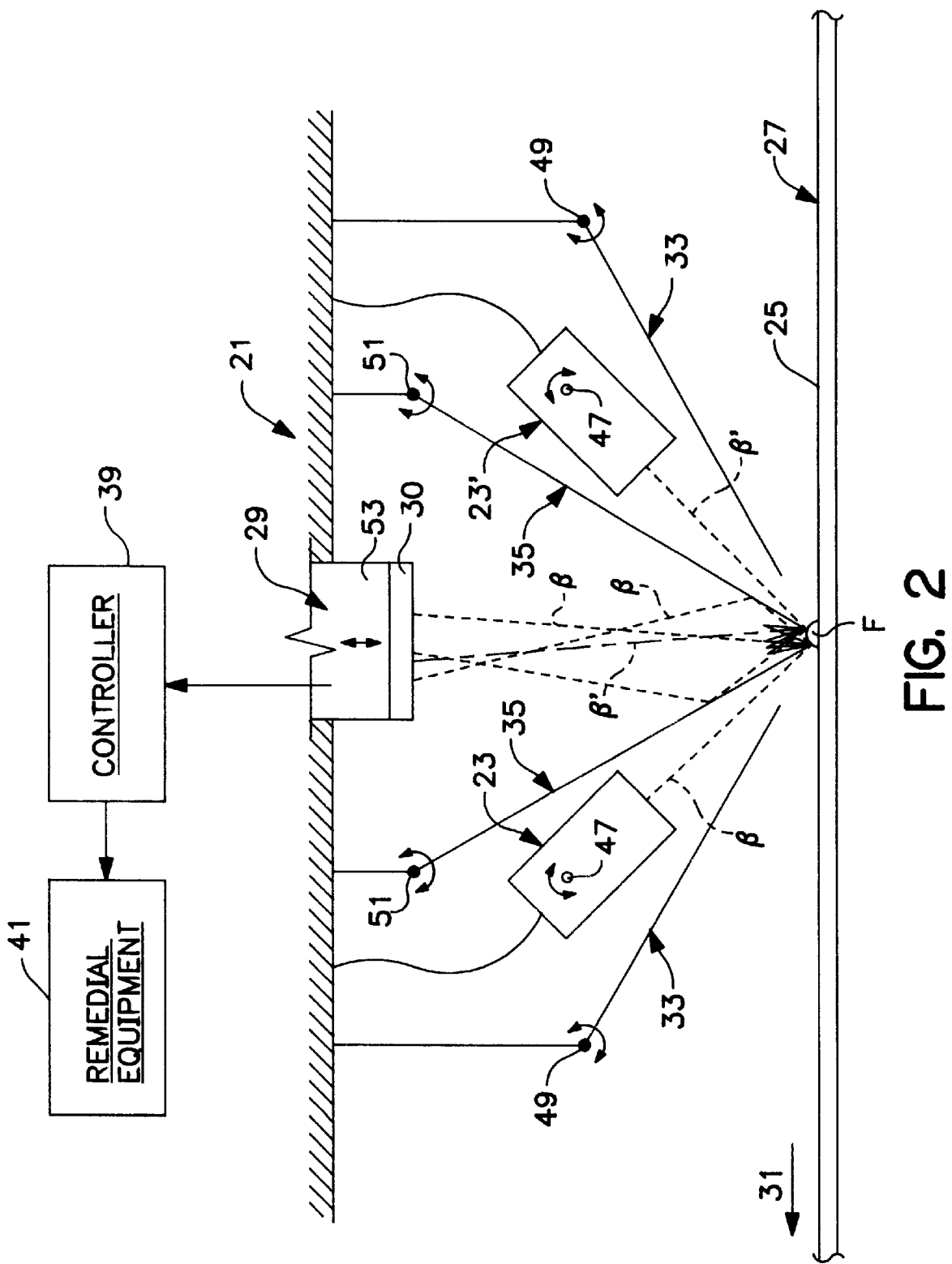
FIG. 2 is a schematic, partially cross-sectional, side view of an apparatus according to the present invention showing normal operation with material having a flaw the form of a surface protrusion.
Figure 3:
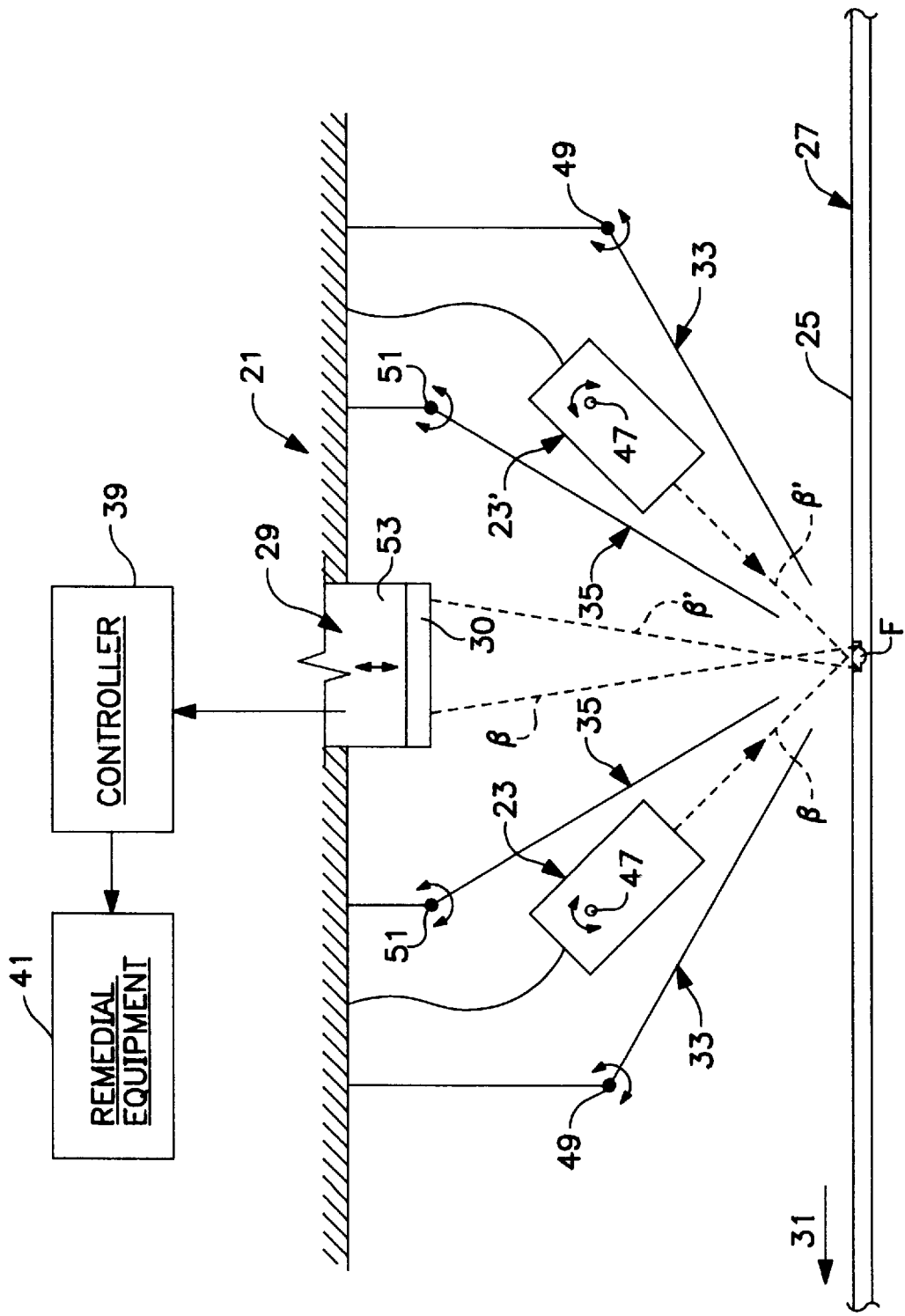
FIG. 3 is a schematic, partially cross-sectional, side view of an apparatus according to the present invention showing normal operation with material having a flaw in the form of a surface recess.

A preferred embodiment of the apparatus 21 for the detection of surface flaws in material having a surface which is partially reflective according to the present invention is shown in FIG. 1. The apparatus 21 includes at least one light source 23 arranged to direct incident light B on a surface 25 of an at least partially reflective material 27, preferably a sheet or web of material that is moved relative to the light source. A light detector 29 is disposed above the surface 25 of the material 27. The light detector 29 and the light source 23 are arranged relative to each other such that, in the absence of a surface flaw in the material, i.e., when the material is substantially flat, substantially no light B from the light source is detected the light detector. However, as seen in FIGS. 2 and 3, when a surface flaw F is present in the material 27, light B from the light source 23 is reflected off of the flaw and into the detector 29. The flaw F may be in the nature of, for example, a protrusion, a hole or recess, or some form of delamination-type flaw that disrupts an otherwise substantially flat surface 25 of the material 27.

Suitable light sources 23 include those in the form of a single light source or, as seen in FIG. 1, two light sources, or more. Multiple light sources 23 may be arranged on opposite sides of the detector 29. If desired or necessary, the light source 23 may include a plurality of light sources, such as where the light source includes a plurality of fiber optic light sources arranged relative to the material 27 to illuminate the surface 25 of the material. In rough applications where only the largest of flaws need be defected, a single illuminating light source 23 may be all that is necessary. However, improved quality assurance may be provided b increasing the number of light sources 23 per detector may be varied. Normally, a single pair, two pairs, or three pairs of light sources 23 is sufficient for good results.

Suitable light detectors 29 include those in the form of a line-scan camera, preferably where the material 27 is relatively wide, such as a charge coupled device, or the light source may be in the form of a photo detector. Photo detectors are convenient where image formation is not necessary, particularly because the circuitry required to operate photo detectors is generally less complex than that used for camera-type systems. The light detector 29 may include a lens 30. The lens 30 may assist in, among other things, detecting faint light reflected from minor flaws F.

The nature of the light emitted from the light source can be different depending upon the nature of the application to which the apparatus 21 will be subjected. For example: light emitted from the light source 23 may be in the form of a focused beam of incandescent light; the light source may emit polarized light; the light source may emit infrared light; and/or the light source may emit ultraviolet light. As desired or necessary, light of different wavelengths or forms may be emitted simultaneously.

The material 27 is preferably flexible and preferably has a highly reflective surfaces, although it will be appreciated that the present invention is applicable to any surface that reflects light. The material 27 is preferably a flexible sheet or web of material that is moved relative to the apparatus 21 in the direction of arrow 31, such as by being drawn by some suitable manner of drawing equipment, such as a pair of rollers between which the material passes, from a rolled web of material, or by moving a sheet of material on a belt. The material 27 is preferably moved at speeds of from about 0.001 m/sec to 2000 m/min and, most preferably, at speeds of between 100 and 800 m/min.

Materials 27 in the form of metallized paper (such as aluminum metallized paper), or aluminum foil, or laminate materials preferably having outer layers of metallized paper or aluminum foil, are particularly preferred for use in connection with the apparatus and method of the present invention. The sheet material 27 may be of widely variable width, such as from a few millimeters to several meters in width, and may be of a widely variable thickness. For example, the material 27 is from 0.5–10 mm in thickness, and more preferably between 1–5 mm. This invention is particularly well suited for paper-foil laminates which are customarily used in cigarette boxes to wrap or otherwise enclose cigarette products. When such laminates come into contact with liquid, either by spraying or droplets failing onto the surface, delamination may occur, necessitating rejection of the delaminated material to ensure proper packaging of products.

The apparatus 21 preferably includes external light baffles 33 arranged relative to the light source 23 and the light detector 29 to exclude ambient light from the light detector. As seen in FIG. 1, the external light baffles 33 are preferably arranged to substantially enclose both the light source 23 and the light detector 29 and, together with the material 27 passing closely beneath the external light baffles, preferably exclude substantially all ambient light from the light detector.

The apparatus 21 preferably also includes internal light baffles 35 arranged relative to the light source 23 and the light detector 29 to exclude light from the light source from the light detector except in the presence of a flaw in the material. As seen in FIG. 1, the internal light baffles 35 are preferably arranged between the light source 23 and the light detector 29. The external light baffles 33 and the internal light baffles 35 are preferably arranged to substantially surround the light source 23 such that only light reflecting off of flaws F within a small scan zone 37 on the surface 25 of the material 27 is capable of being detected by the detector 29. In the presently preferred embodiment, both external and internal light baffles 33 and 35 are provided, however, if desired or necessary, the external light baffles can be used without the internal light baffles, the internal light baffles can be used without the external light baffles, or no light baffles can be provided at all.

In a method for the detection of flaws F in material 27 according to the present invention shown in FIG. 1, the material 27 having a reflective surface 25 is moved in a direction 31 parallel to the reflective surface. The light source 23 and the light detector 29 are arranged relative to each other and light B is emitted from the light source and onto the reflective surface 25 as the reflective surface is moved such that, when no flaw is present in the reflective surface, no light is detected by the light detector. Light B reflected from flaws F on the reflective surface 25 are detected with the detector 29.

Upon detection of light B by the detector 29, which is indicative of the presence of a flaw F in the surface 25 of the material 27, a signal from the detector is sent to a controller 39 to indicate the presence of a flaw on the surface. The controller 39 preferably controls other known equipment 41 for taking corrective measures, such as by providing a signal to the equipment 41 for marking the material 27 for repair or cutting the material so that it can be removed from subsequent processing operations.

In "no-flaw" operation, the light source 23 emits a first, preferably coherent beam of light B. The first light beam B strikes the surface 25 at a point 43. A second light source 23', if provided, emits a second, preferably coherent light beam B' that preferably also strikes point 43 on the surface 25 of the material 27. Where no flaws are present, the light sources 23, 23' are preferably angled such that the light beams B, B' incident on the surface 25 reflect outside of the internal baffles 35, preferably inside of the external baffles 33, such that little or no light is permitted to enter the detector 29.

FIGS. 2 and 3 illustrate flaw detection at work where the flaw F is in the form of a protrusion and a recess, respectively. The first light source 23 emits a first light beam B that strikes flaw F and is reflected, generally in a diffuse manner, such that a portion thereof enters between the internal baffles 35 and is detected by the detector 29. Likewise the second light source 23' emits a second light beam B' that is also reflected, generally in a diffuse manner, from the flaw F and a portion thereof enters between the internal baffles. The first and/or the second light beams B and/or B' may, when inside of the internal baffles 35, further reflect off of one or both of the internal baffles prior to being detected by the detector 29. Of course, it is possible that, for a given flaw F, only one or part of a plurality of light beams incident on the flaw will actually enter the internal baffles 35. As the flaw F is preferably constantly moving relative to the apparatus, the beams, reflection, and scatter from the flaw will be constantly changing, but at least some portion will be detected by the detector 29. The detector 29 preferably sends a signal to the controller 39 which controls other equipment to address the flaw. For example, the detector 29 may be configured to send a signal into a memory of a controller 39 which recognizes the presence of a flaw and rejects the surface 25 or portion of the material through an indexing process.

The sensor 29 is preferably mounted such that it is in close proximity to the material 27, preferably within about 0.5 cm from the material and, more preferably, within about 0.5–3 mm from the material. The light source 23 is preferably adjustably mounted, such as by being pivotable about an axle 47, to permit adjustment of the angle with which the light B is incident on the material 27. Similarly, the external and internal baffles 33 and 35 are preferably angularly adjustable and/or adjustable in terms of distance from the light source 23 and/or the detector 29 and/or the material 25, such as by being pivotable about axes 49 and 51, respectively. Through appropriate adjustment of the position and/or angle of the light source 23 and/or baffles 33 and 35, use of the apparatus 21 with materials of different thickness, or with materials that are disposed at different distances from the apparatus is facilitated. If desired or necessary, the position and/or angle of the detector 29 is adjustable, such as by providing a telescoping assembly 53. Appropriate adjustment of the components of the apparatus 21 is intended to ensure that a normally reflected (flawless) light beam B does not impinge on the detector 29 while a beam reflect off of a flaw F is detected.

Figure 4:
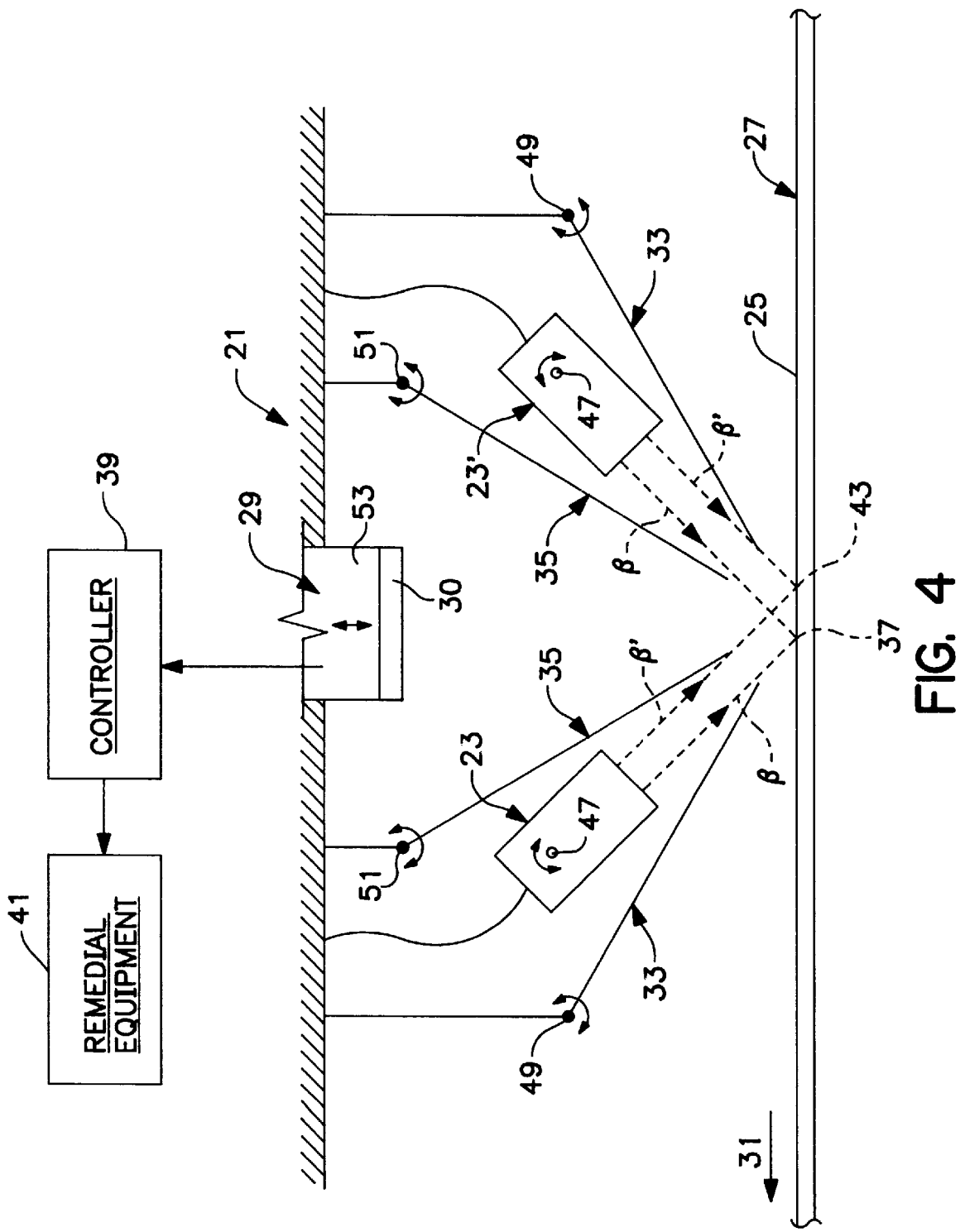
FIG. 4 is a schematic, partially cross-sectional, side view of an apparatus according to another embodiment the present invention showing normal operation with material having no flaws.

As seen in the embodiment of the apparatus 21' shown in FIG. 4, the incident light B and B' from different light sources 23 and 23' need not be focused on the same point as described above with regard to FIGS. 1–3. Light sources 23 and 23' may, for example, focus on different points 43 and 43', respectively, with both points being within the scan zone of the detector 29.

While this invention has been illustrated and described in accordance with a preferred embodiment, it is recognized that variations and changes may be made therein without departing from the invention as set forth in the claims.

What is claimed is:

1. An apparatus for the detection of surface flaws in a moving sample of material having a surface which is partially reflective, the apparatus comprising:

means for moving a sample of material, the material having a surface which is at least partially reflective;

at least one light source arranged to direct incident light on the surface of the material;

a light detector disposed above the surface of the material;

light baffles arranged relative to the at least one light source and the light detector to exclude light from the at least one light source from the light detector except in the presence of a flaw in the material, the light baffles being angularly adjustably mounted relative to a direction of movement of the material, wherein the light detector and the at least one light source are arranged relative to each other such that, in the absence of a surface flaw in the material, substantially no light from the at least one light source is detected by the light detector and, in the presence of a surface flaw in the material, light from the at least one light source is reflected off of the flaw and into the detector.

2. The apparatus as set forth in claim 1, wherein the at least one light source includes two light sources.

3. The apparatus as set forth in claim 1, wherein the at least one light source includes a plurality of light sources.

4. The apparatus as set forth in claim 1, wherein the at least one light source emits a focused beam of incandescent light.

5. The apparatus as set forth in claim 1, wherein the at least one light source emits polarized light.

6. The apparatus as set forth in claim 1, wherein the at least one light source emits infrared light.

7. The apparatus as set forth in claim 1, wherein the at least one light source emits ultraviolet light.

8. The apparatus as set forth in claim 1, wherein the light detector includes a line-scan camera.

9. The apparatus as set forth in claim 1, wherein the light detector is a charge coupled device.

10. The apparatus as set forth in claim 1, wherein the light detector is a photo detector.

11. The apparatus as set forth in claim 1, wherein the light detector is adjustably mounted relative to the at least one light source.

12. The apparatus as set forth in claim 11, wherein the at least one light source is adjustably mounted relative to the light detector.

13. The apparatus as set forth in claim 1, wherein the at least one light source is adjustably mounted relative to the light detector.

14. An apparatus for the detection of surface flaws in a reflective material comprising:

a plurality of fiber optic light sources arranged relative to a reflective material to illuminate the surface of the material;

a line-scan camera facing a surface of the material;

light baffles separating the light sources and the camera;

wherein, when the material is moved relative to the camera and no flaw in the material is present, light from the light sources is reflected off of the material and is blocked by the baffles such that no light from the light sources is detected by the detector, and when a flaw in the material is present, light from the light sources is reflected off of the flaw such that the baffles do not block the reflected light and the reflected light is detected by the detector, an angle of the light baffles relative to a direction of movement of the material being adjustable.

15. A method for the detection of flaws in material, comprising the steps of:

moving a material having a reflective surface in a direction parallel to the reflective surface;

arranging at least one light source and a light detector relative to each other, and emitting light from the at least one light source and onto the reflective surface as the reflective surface is moved such that, when no flaw is present in the reflective surface, no light is detected by the light detector;

detecting light reflected from one or more flaws on the reflective surface with the detector;

excluding light emitted by the at least one light source from the light detector except in the presence of a flaw in the material with light baffles arranged relative to the at least one light source and the light detector; and adjusting an angle of the light baffles relative to the material.

16. The method as set forth in claim 15, comprising the further step of sending a signal from the detector to a controller to indicate the presence of a flaw on the reflective surface.

17. The method as set forth in claim 15, wherein the at least one light source emits a focused beam of incandescent light.

18. The method as set forth in claim 15, wherein the at least one light source emits polarized light.

19. The method as set forth in claim 15, wherein the at least one light source emits infrared light.

20. The method as set forth in claim 15, wherein the at least one light source emits ultraviolet light.

21. The method as set forth in claim 15, comprising the further step of excluding ambient light from the light detector.

22. The method as set forth in claim 21, wherein light from the at least one light source is excluded from the light detector except in the presence of a flaw in the material by light baffles arranged relative to the at least one light source and the light detector.

23. The method as set forth in claim 15, comprising the further step of adjusting a position of the at least one light source relative to the light baffles and the light detector.

24. The method as set forth in claim 15, comprising the further step of adjusting a position of the light detector relative to the at least one light source and the light baffles.

25. The method as set forth in claim 15, comprising the further step of adjusting a position of the at least one light source relative to the light detector.

26. The method as set forth in claim 15, comprising the further step of adjusting a position of the light detector relative to the at least one light source.

* * * * *